(12) United States Patent
Proctor

(10) Patent No.: US 8,778,969 B2
(45) Date of Patent: Jul. 15, 2014

(54) NITRONE, NITROSO, AND NITROXIDE SPINTRAPS AND SPIN LABELS AND THEIR HYDROXYLAMINES

(76) Inventor: Peter H Proctor, Houston, TX (US)

( * ) Notice: Subject to any disclaimer, the term of this patent is extended or adjusted under 35 U.S.C. 154(b) by 446 days.

(21) Appl. No.: 12/941,071

(22) Filed: Nov. 7, 2010

(65) Prior Publication Data

US 2012/0115905 A1     May 10, 2012

Related U.S. Application Data

(60) Provisional application No. 61/259,138, filed on Nov. 7, 2009.

(51) Int. Cl.
    *A61K 31/445*     (2006.01)
    *C07D 211/94*     (2006.01)

(52) U.S. Cl.
    USPC ............... 514/315; 546/184; 546/242

(58) Field of Classification Search
    USPC ........................................ 514/315
    See application file for complete search history.

(56) References Cited

U.S. PATENT DOCUMENTS

| | | |
|---|---|---|
| 5,714,482 A | 2/1998 | Proctor |
| 5,714,510 A | 2/1998 | Proctor |
| 5,716,947 A | 2/1998 | Proctor |
| 5,728,714 A | 3/1998 | Proctor |
| 6,262,042 B1 * | 7/2001 | Cook et al. ............... 514/177 |
| 6,617,337 B1 | 9/2003 | Wilcox |
| 6,835,754 B2 | 12/2004 | Waterbury et al. |
| 7,115,666 B2 | 10/2006 | Khan et al. |
| 7,285,544 B2 | 10/2007 | Bernstein |
| 7,314,633 B2 | 1/2008 | Hsia et al. |
| 7,442,711 B2 | 10/2008 | Matier et al. |
| 7,589,107 B2 | 9/2009 | Matier et al. |
| 7,625,928 B2 | 12/2009 | Maxwell et al. |
| 2008/0280890 A1 | 11/2008 | Patil |
| 2008/0319014 A1 | 12/2008 | Habash et al. |
| 2010/0035869 A1 | 2/2010 | Wipf et al. |
| 2010/0041716 A1 | 2/2010 | Habash et al. |
| 2010/0168112 A1 | 7/2010 | Kelly et al. |

OTHER PUBLICATIONS

Santen et al., "Benign Breast Disorders", N. Engl. J. Med., 353, 3, 275-285; see particularly p. 281 paragraphs 3-5.*
Lala et al., Role of nitric oxide in carcinogenesis and tumour progression, The Lancet Oncology, 2001, 2, 3, 149-156.*
Preti et al., The Superoxide Dismutase Mimetic, Tempol, Reduces the Bioavailability of Nitric Oxide and does not Alter L-NAME-Induced Hypertension in Rats, Basic & Clinical Pharmacology & Toxicology, 2005, 97, 29-34.*

* cited by examiner

*Primary Examiner* — Sreeni Padmanabhan
*Assistant Examiner* — Jason A Deck

(57) ABSTRACT

Nitrone, nitroso, and nitroxide spintraps and spin labels and their reduction products are claimed for the prevention and treatment of fibrocystic disease of breast, premenstrual dysphoric syndrome and associated symptomology, prevention and treatment of migraine headache, cyclic vomiting syndrome, rectal hemorrhoids, trigeminal neuralgia, peripheral vascular disease, influenza, peridontitis and gingivitis, herpes zoster, herpes simplex, and post-herpetic neuralgia.

3 Claims, No Drawings

NITRONE, NITROSO, AND NITROXIDE SPINTRAPS AND SPIN LABELS AND THEIR HYDROXYLAMINES

U.S. Provisional Application No. 61/259,138, filed Nov. 7, 2009.

BACKGROUND OF THE INVENTION (1) Field of Invention
Treatment of Fibrocystic Disease of Breast
(2) Description of Related Art

CITATIONS

Cuscela, Daniel, et al. "Protection from Radiation-Induced Alopecia with Topical Application of Nitroxides: Fractionated Studies", The Cancer Journal from Scientific American, 1996; vol. 2, No. 5, pp. 273-278.
Santen R J, Mansel R. Benign breast disorders. N Engl J Med. 2005; 353(3):275-85. Review.
Shuaib A, Lees K R, Lyden P, Grotta J, Davalos A, Davis S M, Diener H C, Ashwood T, Wasiewski W W, Emeribe U. NXY-059 for the treatment of acute ischemic stroke. *N Engl J Med.* 2007; 357: 562-571
Proctor P H, Tamborello L P. SAINT-I worked, but the neuroprotectant is not NXY-059. Stroke. 2007 October; 38(10):e109
Proctor P H. Uric acid and neuroprotection. Stroke. 2008 August; 39(8):e126. Augusto O, Trindade D F, Linares E, Vaz S M. Cyclic nitroxides inhibit the toxicity of nitric oxide-derived oxidants: mechanisms and implications. An Acad Bras Cienc. 2008 March; 80(1):179-89.
Wilcox C S, Pearlman A. Chemistry and antihypertensive effects of tempol and other nitroxides. Pharmacol Rev. 2008 December; 60(4):418-69.
Simonsen U, Christensen F H, Buus N H. The effect of tempol on endothelium-dependent vasodilatation and blood pressure. Pharmacol Ther. 2009 May; 122(2):109-24.
Kamat C D, Gadal S, Mhatre M, Williamson K S, Pye Q N, Hensley K. Antioxidants in central nervous system diseases: preclinical promise and translational challenges. J Alzheimers Dis. 2008 November; 15(3):473-93.
Floyd R A. Serendipitous findings while researching oxygen free radicals. Free Radic Biol Med. 2009 Apr. 15; 46(8): 1004-13.
Wilcox C S. Effects of tempol and redox-cycling nitroxides in models of oxidative stress. Pharmacol Ther. 2010 May; 126(2):119-45.

Various publications, including patents, published applications, and scholarly or technical articles are cited above and throughout the specification. Each of the cited publications is incorporated by reference herein, in its entirety.

Fibrocystic disease of the breast in women is a chronic potentially-debilitating disease associated with significant morbidity, especially pain and discomfort (Santen R J, Mansel R. Benign breast disorders. N Engl J Med. 2005; 353(3):275-85). Generally considered a benign condition, the existence of breast cysts can interfere with the diagnosis of breast cancer. To date, other than simple palliation with analgesics and hormonal drugs, the only treatment per se for fibrocystic disease of breast has been surgical excision of the cysts. In some cases, this can include complete mastectomy.

The efficacy of various nitron, nitroso, and nitroxide spin traps and spin labels and their equivalent reduction products in some model diseases in experimental animals has long been recognized. For reviews, see: Wilcox C S. Effects of tempol and redox-cycling nitroxides in models of oxidative stress. Pharmacol Ther. 2010 May; 126(2):119-45, Wilcox C S, Pearlman A. Chemistry and antihypertensive effects of tempol and other nitroxides. Pharmacol Rev. 2008 December; 60(4):418-69, Simonsen U, Christensen F H, Buus N H. The effect of tempol on endothelium-dependent vasodilatation and blood pressure. Pharmacol Ther. 2009 May; 122(2): 109-24., Floyd R A. Serendipitous findings while researching oxygen free radicals. Free Radic Biol Med. 2009 Apr. 15; 46(8):1004-13. Wilcox C S. Effects of tempol and redox-cycling nitroxides in models of oxidative stress. Pharmacol Ther. 2010 May; 126(2):119-45. However, studies with such antioxidant drugs have not well translated to humans. E.g., with respect to neuroprotection and cardioprotection in general and nitrone and nitroxide drugs in particular: "There are hundreds, perhaps thousands of neuroprotective drugs that have been used in animal models. So, if you were a mouse or a rat, and experienced a stroke or cardiac arrest, we would know just what to do for you. But, essentially none of these pharmacological agents have demonstrated usefulness in humans even though they have been shown to be successful in preclinical animal trials" (Traystman R J. Neuroprotection: introduction. Stroke. 2010 October; 41(10 Suppl):S63.). In particular, one such neuroprotective agent effective in animal models, but not in humans, is the phenybutylnitrone derivative NXY-059 (Shuaib A, Lees K R, Lyden P, Grotta J, Davalos A, Davis S M, Diener H C, Ashwood T, Wasiewski W W, Emeribe U. NXY-059 for the treatment of acute ischemic stroke. *N Engl J Med* 2007; 357: 562-571). Moreover, in animals treatment effects are reported at systemic human equivalent doses orders of magnitude higher than we found efficacy in (e.g.) fibrocystic disease in humans. If the in vivo active form is (say) the reduced derivative, this may be an unexpected consequence of the presence in humans and higher primates of singularly high levels of the powerful reducing substance uric acid. Paradoxically, since it competes with them for action, the singularly-high level of urate in humans may also may explain the perpetual failure of antioxidant drugs such as NXY-059 in human clinical trials, even at several grams per day doses (Proctor P H. Uric acid and neuroprotection. Stroke. 2008 August; 39(8):e126.). That is, any systemic efficacy of such nitrone, nitroso, and nitroxide drugs in humans, much less efficacy at very low doses, is unexpected.

Similarly, we recognized the potential benefit of administering such compounds topically in their reduced forms (U.S. Pat. Nos. 5,714,482, 5,714,510, 5,716,947, 5,723,502, 5,728, 714), e.g., in presence of a strong reducing compound such as ascorbic acid. For one thing, coadministration in the reduced form or in the presence of a reducing substances may prevent depletion of endogenous reducing equivalents by the parent drugs. These patents are here-by incorporated by reference. However, the efficacy, much less the benefits, of the using such reduced forms is disputed. E.g., Hsia et al (U.S. Pat. No. 7,314,633) note that "If a nitroxide is reduced to a hydroxylamine it loses its ability to modulate reactions. By positioning the nitroxide between two carboxylic acid groups a "gating" effect is obtained, i.e. the nitroxide is protected and its ability to modulate reactions is maintained over a longer period of time in a greater range of in vivo environments as compared to a molecule lacking the carboxylic acid groups."

Moreover, because there is no good animal model for fibrocystic disease of breast, such agents have never been considered for the treatment of this condition. In fact, previously, the only human use of (e.g.) TEMPOL was experimental topical treatment to ameliorate radiation injury (Cuscela, Daniel, et al. "Protection from Radiation-Induced Alopecia with Topical Application of Nitroxides: Fractionated Studies", The Cancer Journal from Scientific American, 1996; vol. 2, No. 5, pp. 273-278.).

However, in the course of extemporaneous treatment with an oral formulation of the reduced form of TEMPOL (TEMPOL-H), we unexpectedly observed and documented almost complete regression of long-standing and intractable fibrocystic disease in a 48-year-old female patient. Upon cessation of treatment, the clinical signs and symptoms of fibrocystic disease reappeared within a few weeks. Upon resumption of treatment, they again regressed.

BRIEF SUMMARY OF THE INVENTION

The present invention is directed to methods that treat, inhibit, or slow the development of fibrocystic disease of breast. The inventive methods comprise the administration of pharmaceutical preparations comprising nitrone, nitroxide and nitroso compounds and their corresponding reduction products orally, intraorally, systemically by injection, or by local rectal administration.

DESCRIPTION OF THE INVENTION

Definitions

The term "nitroxide", "nitrone", and "nitroso" are used herein to describe molecules comprising an oxygen and a nitrogen atom directly bound to each other. These compounds may be a electron donors or acceptors. Depending on their oxidation state, these compounds may comprise stable nitroxyl free radicals including precursors (such as the N—H form), and derivatives thereof including their corresponding hydroxylamine derivative (N—OH), where the oxygen atoms are replaced with a hydroxyl group and/or exist in a hydrogen halide form. Nitroxides and nitrones of the invention may be administered to a system, such as a human, and act to modulate oxidation and reduction reactions by donating or accepting an electron. Other mechanisms may include formation of charge-transfer complexes as well as by "redox signaling" or modulation of redox-signaling-mediated processes. Stability of unpaired electrons on such compounds is typically-provided at the nitrogen nucleus by two adjacent carbon atoms that may be substituted with strong electron donor groups. With the partial negative charge on the oxygen of the N—O bond, the two adjacent carbon atoms together localize the unpaired electron on the nitrogen nucleus. Nitroxides and nitrones generally may have either a heterocyclic or a linear structure. In an in vivo environment a nitroxide may react with a first superoxide to form oxoammonium (as an electron donor) and then react with a second superoxide to re-form the nitroxide (as an electron acceptor). (Review: Wilcox C S. Effects of tempol and redox-cycling nitroxides in models of oxidative stress. Pharmacol Ther. 2010 May; 126(2):119-45.)

The terms "treat," "treatment" and the like are used herein to generally mean obtaining a desired pharmacological and/or physiological effect in humans or other animals. A treatment is an approach for obtaining beneficial or desired clinical results. While the claims are not dependent on any specific mechanism, in the present case, these clinical results include but are not limited to decreasing undesirable effects of reactive oxygen species (ROS) and oxidative stress in general, as well as modulating more specific messenger processes such as "redox signaling". The effect may be therapeutic in terms of a partial or complete cure of the disease and/or adverse effect attributed to the disease. In general, methods of the invention may be applied to a variety of different areas including the skin, mucus membranes including those in the GI tract, nose, throat, mouth, vaginal cavity, ocular surfaces, as well as the surfaces of the lungs and the surfaces of the vascular system ans well as systemically by means of intravenous, intraocular, intramuscular, transdermal, sublingual, and/or intraoral administration. "Treatment" as used herein covers any treatment of such a symptom or disease in a mammal, particularly a human, and includes:

(a) inhibiting the disease, i.e. arresting it's development; or
(b) relieving the disease and/or it's symptom, i.e. causing regression of the disease and/or the symptoms caused by the disease.

Exemplar Nitrone and nitroxide spin traps and spin labels include, but are not limited to, DEPMPO (5-(Diethoxyphosphoryl)-5-methyl-1-pyrroline N-oxide), TEMPO (2,2,6,6-tetramethyl-1-piperidinyl-1-oxyl), 4-Amino-TEMPO, 4-hydroxy-TEMPO (TEMPOL), DMPO (5,5-dimethylpyrroline-N-oxide), EMPO (2-Ethoxycarbonyl-2-methyl-3,4-dihydro-2H-pyrrole-1-oxide), POBN (alpha-(4-pyridyl-1-oxide)-N-tert-butylnitrone), TEMPONE (4-oxo-2,2,6,6-tetramethylpiperidine-1-oxyl 4-Oxo-TEMPO), TMIO, 3,3,5,5 tetramethyl-1-pyrolline-N-oxide (TMPO), M3PO (2,5,5-trimethyl-1-pyrroline-N-oxide), M4PO (3,3,5,5-tetramethyl-1-pyrroline-N-oxide), TMPO (3,3,5,5 tetramethyl-1-pyrolline-N-oxide), PBN (1-alpha-phenyl-tert-butyl nitrone), and MNP (2-methyl-2-nitrosopropane), as well as their corresponding hydroxylamine derivatives. The various sulfone (e.g., NXY-059, disulfonyl PBN), hydroxyl, and other derivatives such as esters, peptides, hydroxyl, hydroxylamines, nitrones, carboxyls, and so forth are also claimed.

Preferred examples of the type of hydroxylamine compounds suitable for use in the present invention are TEMPOL-H ((the hydroxylamine reduced form of the nitroxide 4-hydroxy-2,2,6,6-tetramethylpiperidin-1-yloxy), TEMPO-H (the hydroxylamine reduced form of the nitroxide 2,2,6,6-tetramethylpiperidin-1-yloxy) and OXANO-H (2-ethyl-2,4,4-trimethyloxazolidine, which is the reduced form of oxano, 2-ethyl-2,4,4-trimethyloxazolidin-3-yloxy). Other hydroxylamine compounds suitable for use in the present invention include, but are not limited to, those disclosed by Hahn et al. (1998, supra; 2000, supra), Samuni et al. (2001, supra); and in U.S. Pat. No. 5,981,548 to Paolini, et al. (disclosing certain N-hydroxylpiperidine esters and their use as antioxidants in a number of contexts); U.S. Pat. No. 4,404,302 to Gupta et al. (disclosing the use of certain N-hydroxylamines as light stabilizers in plastics formulations); U.S. Pat. No. 5,462,946 to Mitchell et al. (disclosing certain nitroxides deriving from substituted oxazolidines for protection of organisms from oxidative stress); U.S. Pat. No. 3,936,456 to Ramey et al. (disclosing substituted piperazine dione oxyls and hydroxides for the stabilization of polymers); U.S. Pat. No. 4,691,015, to Behrens et al. (describing hydroxylamines derived from hindered amines and the use of certain of them for the stabilization of polyolefins); and the hydroxylamine compounds disclosed in the several aforementioned U.S. patents to Hsia et al. Most of the above-referenced compounds have not been known heretofore for administration to humans. Certainly, none of them has been known for use in the treatment of fibrocystic disease of the breast.

Suitable reducing agents include, but are not limited to: ascorbic acid, lipoic acid, cystine, purines and derivatives such as acetylcysteine, uric acid and other oxyxanthines, methionine, homocysteine, NADPH, NADH, and so forth.

EXAMPLES

Preparation of a Therapeutic Solution of Reduced TEMPOL

The reduced form of TEMPOL (TEMPOL-H) or equivalent pharmacologically-active spin label/spintrap is prepared by mixing together 2 grams of TEMPOL or a pharmacologically effective amount of another spin-label or spin trap such as methynitrosopropane, 20 grams of ascorbic acid or other reducing compound in 100 ml of distilled water. The formulation is used as is. The solution is slightly-bitter. The formulation can be administered diluted in a suitable liquid such as juice, tea, or coffee. An equivalent dry form as 10 mg of tempol mixed with 100 mg of ascorbic acid or equivalent reducing substance can be easily prepared in capsule or tablet form.

Treatment of Fibrocystic Disease of Breast.

One-half ml of the above solution, comprising 10 mg TEMPOL plus 100 mg ascorbic acid, was administered orally once a day to a 50 kg woman with a long history for fibrocystic disease of breast so severe that surgeons had recommended mastectomy. The same person had also been previously-diagnoses with severe trigeminal neuralgia.

First results appeared after 1-2 weeks of treatment and involve shrinkage of the breast cysts, as verified by before and after mammographic imaging, and digital palpation. Long-term relief can be achieved, but the symptoms eventually reappear on cessation of treatment for a few weeks. Upon resumption of treatment, symptoms the breast cysts again drastically shrink. Alternate forms of oral administration such as tablets, pills or capsules are also effective. Parental modes of administration such as intravenous, intramuscular, subcutaneous, intraperitoneal, transrectal and so forth are also possible, as are topical modes of administration such as in lotions, creams, gels, and topically-compatible suspensions and solutions. Tempol itself is effective at the same doses, but may have increased side-effects at higher doses, e.g., due to oxidation of reducing agents or production of hydrogen peroxide.

Such methods that are routine in the art, and may vary with the needs of individual subjects. The present invention is not limited to the embodiments described and exemplified above, but is capable of variation and modification within the scope of the appended claims. Also, the claims are not bound by any suggested possible mechanism of action and are independent thereof.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention. Likewise, each claim and indication stands independent of the patentability or patent status of any other claim and indication.

What is claimed is:

1. A method of treating fibrocystic disease of breast comprising administering to a patient in need thereof a therapeutically effective amount of a compound selected from the group consisting of TEMPO (2,2,6,6-tetramethyl-1-piperidinyl-1-oxyl), 4-hydroxy-TEMPO (TEMPOL), 4 amino-TEMPO, TEMPO-H, and TEMPOL-H.

2. The method of claim 1 wherein the therapeutically effective amount of a compound selected from the group consisting of TEMPO (2,2,6,6-tetramethyl-1-piperidinyl-1-oxyl), 4-hydroxy-TEMPO (TEMPOL), 4 amino-TEMPO, TEMPO-H, and TEMPOL-His 0.01-1000 mg per day administered orally, sublingually, transrectally, intramuscularly, intravenously, or subcutaneously.

3. The method of claim 1 wherein the therapeutically effective amount of a compound selected from the group consisting of TEMPO (2,2,6,6-tetramethyl-1-piperidinyl-1-oxyl), 4-hydroxy-TEMPO (TEMPOL), 4 amino-TEMPO, TEMPO-H, and TEMPOL-His administered along with a reducing agent.

* * * * *